(12) United States Patent
Lee et al.

(10) Patent No.: US 6,589,707 B2
(45) Date of Patent: *Jul. 8, 2003

(54) PARTIALLY CROSSLINKED POLYMER FOR BILAYER PHOTORESIST

(75) Inventors: Geun Su Lee, Kyoungki-do (KR); Jae Chang Jung, Kyoungki-do (KR); Min Ho Jung, Kyoungki-do (JP); Ki Ho Baik, Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 127 days.

This patent is subject to a terminal disclaimer.

(21) Appl. No.: 09/788,181

(22) Filed: Feb. 15, 2001

(65) Prior Publication Data

US 2001/0031420 A1 Oct. 18, 2001

(30) Foreign Application Priority Data

Feb. 18, 2000 (KR) .......................... 2000-7853

(51) Int. Cl.⁷ .......................... G03F 7/004; C08F 30/08
(52) U.S. Cl. .................. 430/270.1; 430/905; 430/910; 526/279; 526/281; 556/431; 560/120
(58) Field of Search .................. 430/270.1, 312, 430/311, 326, 905, 910; 526/279, 281; 556/431; 560/120

(56) References Cited

U.S. PATENT DOCUMENTS

2001/0031420 A1 * 10/2001 Lee et al. .............. 430/270.1
2002/0028406 A1 * 3/2002 Lee et al. .............. 430/270.1

FOREIGN PATENT DOCUMENTS

WO   WO 8601219 A  * 2/1986  .......... C08L/83/00

* cited by examiner

Primary Examiner—Rosemary Ashton
Assistant Examiner—Yvette C. Thornton
(74) Attorney, Agent, or Firm—Townsend and Townsend and Crew LLP

(57) ABSTRACT

The present invention provides photoresist monomers, photoresist polymers derived from the same, processes for producing such photoresist polymers, photoresist compositions comprising such polymers, and processes for producing a photoresist pattern using such photoresist compositions. In particular, photoresist monomers of the present invention comprise a moiety of Formula 4:

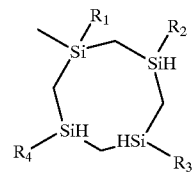

where $R_1$, $R_2$, $R_3$ and $R_4$ are those defined herein. Photoresist polymers of the present invention have a relatively high etching resistance, and therefore are useful in a thin resist process and a bilayer photoresist process. Moreover, photoresist polymers of the present invention have a high contrast ratio between an exposed region and a non-exposed region.

23 Claims, 4 Drawing Sheets

PARTIALLY CROSSLINKED POLYMER FOR BILAYER PHOTORESIST

BACKGROUND OF THE INVENTION

1. Field of the Invention

The present invention relates to photoresist monomers suitable for a bilayer photoresist, polymers derived therefrom and photoresist compositions comprising such polymers. In particular, the present invention relates to photoresist monomers comprising a silicon moiety.

2. Description of the Background Art

Some semiconductor manufacturing processes use photoresist copolymers derived from a monomer comprising an alicyclic compound to form ultrafine patterns. However, the yield of photoresist polymers from these compounds is relatively low resulting in increased manufacturing costs. While the yield of acrylates polymerization is high, the resulting photoresist polymers have a weak etching resistance, thereby limiting its use.

Forming an ultrafine pattern below 0.13 m using a conventional photoresist coating thickness results in a high aspect ratio which may cause the pattern to collapse. And if the coating thickness is reduced, the resulting photoresist coating often has low or no etching resistance. Thus, it is difficult to perform following, or successive processes after etching process using conventional photoresist polymers.

One method for overcoming the above described limitations is to use a "thin resist-hard mask" process, which generally involves reducing a coating thickness of the photoresist composition and introducing a hard mask below the photoresist film coating. Another method is to use a bilayer photoresist comprising silicon, which involves coating a bottom anti-reflective coating material (BARC), g-line photoresist or i-line photoresist on the substrate and then coating a silicon comprising photoresist thereon. The resulting photoresist film is exposed, and the upper layer (i.e., photoresist comprising silicon) is wet developed to form an upper layer photoresist pattern. The lower layer is dry developed using $O_2$ plasma and the upper photoresist pattern as a mask to form a lower layer resist pattern. This process reduces or eliminates the occurrence of photoresist pattern collapse.

SUMMARY OF THE INVENTION

It is therefore an object of the present invention to provide a photoresist monomers comprising silicon, photoresist polymers for bilayer resist derived from the same, and a process for preparing such photoresist polymers.

Another object of the present invention is to provide photoresist compositions comprising such photoresist polymers.

Still another object of the present invention is to provide a semiconductor device produced by using such a photoresist composition.

DETAILED DESCRIPTION OF THE INVENTION

Figure 1:
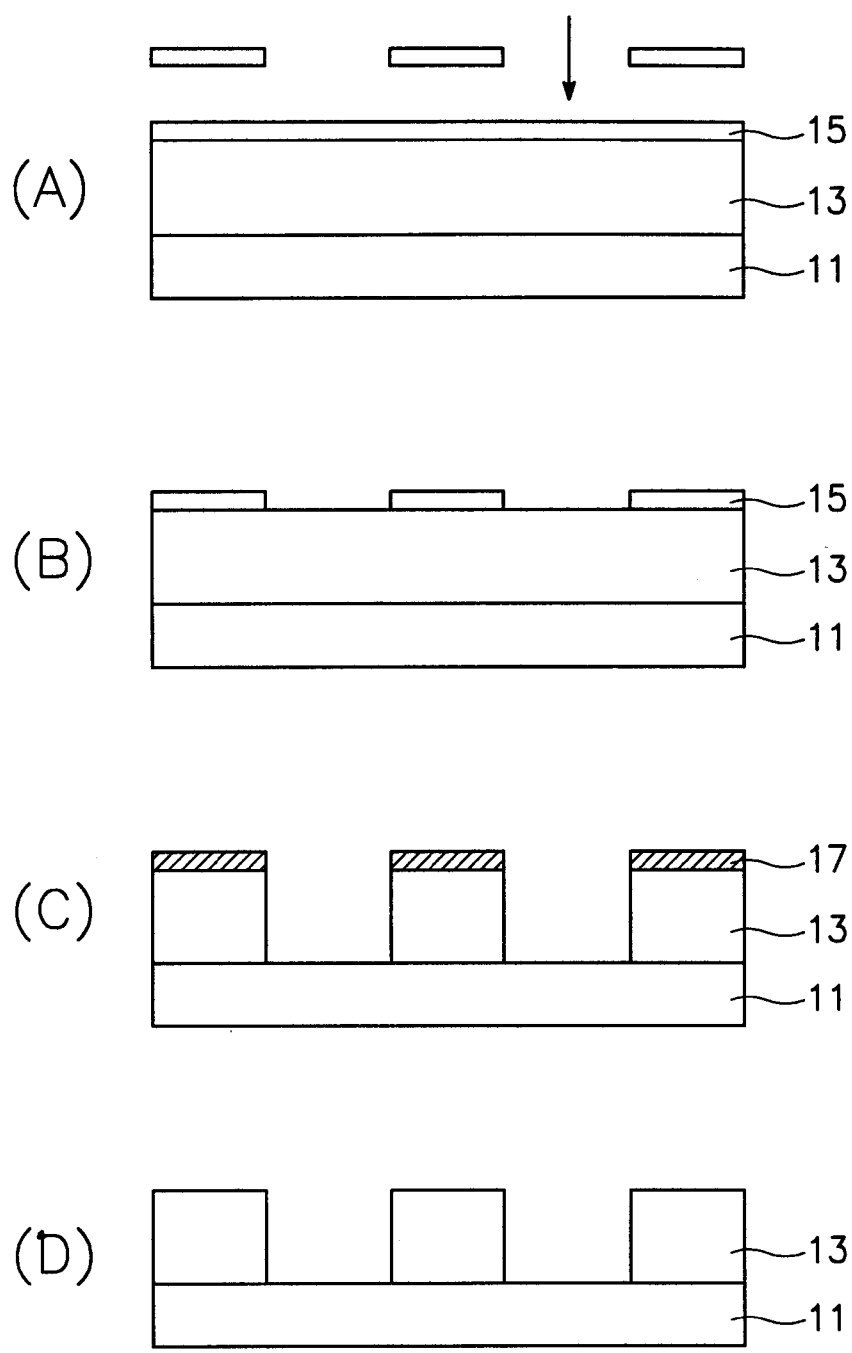
FIG. 1 illustrates a process for forming a photoresist pattern in accordance with a preferred embodiment of the present invention.

One aspect of the present invention provides a photoresist monomer selected from the group consisting of compounds of the formula:

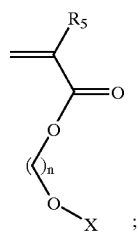

1

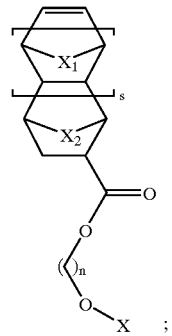

2

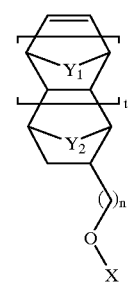

3 where
each of $X_1$, $X_2$, $Y_1$ and $Y_2$ is independently alkylene, preferably methylene or ethylene;

$R_5$ is hydrogen or alkyl, preferably hydrogen or methyl;

s and t are integers from 0 to 2;

n is an integer from 1 to 5; and

X is a moiety of the formula:

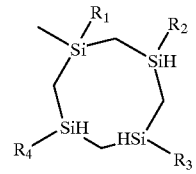

4 where
each of $R_1$, $R_2$, $R_3$ and $R_4$ is independently hydrogen, $C_1$–$C_{10}$ alkyl, or $C_1$–$C_{10}$ alkyl comprising an ether linkage.

In one particular embodiment of the present invention, the photoresist monomers is selected from the group consisting of compounds of the formula:

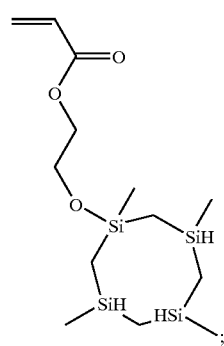

1A

-continued

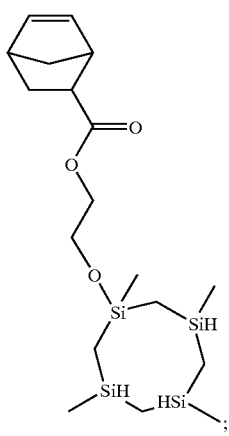

2A

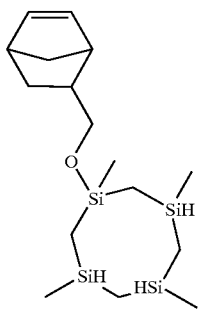

3A

The present invention also provides a photoresist polymer derived from a monomer comprising a first monomer selected from the group consisting of the compounds of Formulas 1 to 3, and mixtures thereof.

Photoresist polymers of the present invention include a monomer comprising a silicon rich moiety of Formula 4. Preferably, photoresist polymers of the present invention comprise from about 7 to about 30 wt % of silicon. Without being bound by any theory, it is believed that an excellent etching resistance to oxygen afforded by the present photoresist polymers is due to the presence of such a relatively high amount of silicon. This etching resistance to oxygen makes photoresist polymers of the present invention useful in a bilayer photoresist process. The present inventors have found that even a thin coating of photoresist polymers of the present invention provides a successful ultrafine pattern formation.

The monomer used to produce photoresist polymers of the present invention can further comprise a second monomer of the formula:

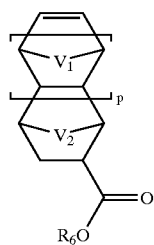

5 where
$V_1$ and $V_2$ are independently alkylene, preferably methylene or ethylene;
$R_6$ is an acid labile protecting group; and
p is an integer from 0 to 2.

The acid labile protecting group may be selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

The monomer used to produce photoresist polymers of the present invention can further comprise a third monomer of the formula:

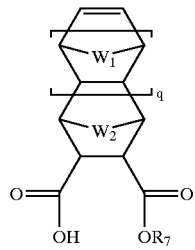

6 wherein
$W_1$ and $W_2$ are independently alkylene, preferably methylene or ethylene;
$R_7$ is $C_1$–$C_{12}$ alkyl comprising an ether linkage or $C_1$–$C_{12}$ alkyl comprising a hydroxyl group; and
q is an integer from 0 to 2.

The monomer used to produce photoresist polymers of the present invention can further comprise a fourth monomer which can provide cross-linkage within the photoresist polymer. Preferably, the fourth monomer is a compound of the formula:

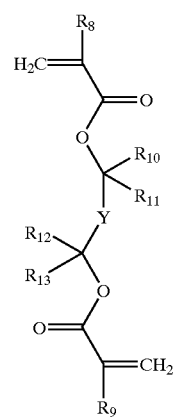

7 where
Y is $C_1$–$C_{12}$ alkylene, oxygen, or $C_1$–$C_{12}$ alkylene comprising an ether linkage;
each of $R_8$ and $R_9$ is independently hydrogen or alkyl, preferably hydrogen or methyl; and
each of $R_{10}$, $R_{11}$, $R_{12}$ and $R_{13}$ is independently H, $C_1$–$C_{12}$ alkyl, or $C_1$–$C_{12}$ alkyl comprising an ether linkage.

The diacrylate crosslinking compound of Formula 7 improves the polymerization yield of the polymer. In addition, the hydrophobic property in a non-exposed region of the photoresist is significantly increased due to the crosslinking. As a result, the developing solution does not remove any significant amount of the photoresist polymer in the non-exposed region, but the photoresist polymer in the exposed region is efficiently removed by the developing solution. Therefore, the contrast ratio between the exposed region and the non-exposed region of photoresist polymers of the present invention is significantly increased.

The monomer used to produce photoresist polymers of the present invention can further comprise maleic anhydride as a fifth monomer. Maleic anhydride also increases the polymerization yield of the polymer.

Furthermore, the monomer used to produce photoresist polymers of the present invention can further comprise a sixth monomer of the formula:

8 where
  Z is alkylene or oxygen, preferably methylene, ethylene or oxygen.

Photoresist polymers of the present invention comprise a number of relatively sterically large substituent groups. Thus, it is preferable to add the compound of Formula 8 having a relatively small steric hindrance as a spacer monomer so as to adjust a molecular weight of the resulting photoresist polymer and to improve the polymerization yield.

In one particular embodiment, polymers of the present invention is selected from the group of consisting of polymers of the formula:

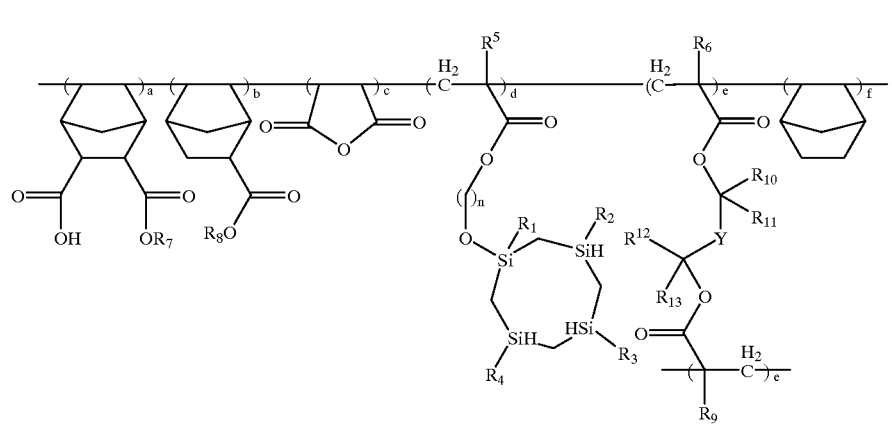
9

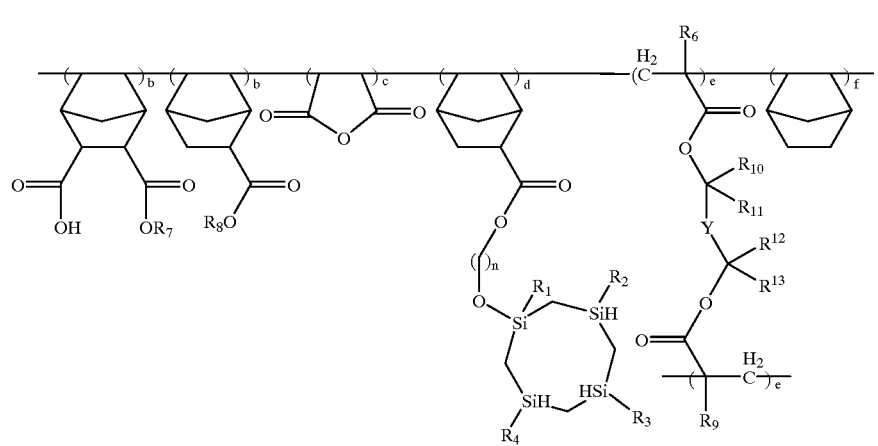
10

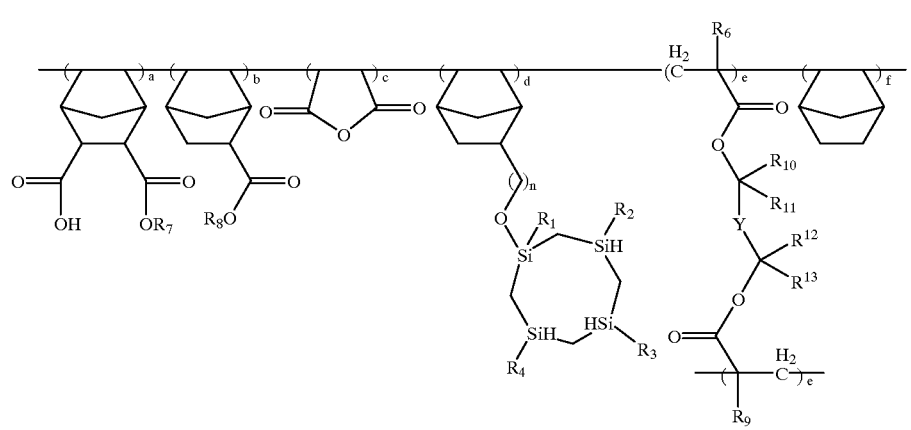
11 wherein $R_1$, $R_2$, $R_3$, $R_4$, $R_5$, $R_6$, $R_7$, $R_8$, $R_9$, $R_{10}$, $R_{11}$, $R_{12}$, $R_{13}$, Y, and n are those defined above; and a, b, c, d, e and f individually denote the mole ratio of each monomer, with proviso that d is not 0.

The terminal groups of polymers depicted in the present disclosure depend on the polymerization initiator and/or the polymerization terminator used. In addition, as used throughout this disclosure, it should be appreciated that the order of monomeric units represented in polymer formulas of the present disclosure does not necessarily indicate the actual order of such monomeric units in the polymers. Monomeric units represented in polymer formulas are intended to simply indicate the presence of such monomeric units in the polymer. Moreover, the variables represent the total relative ratio of each unit. For example, the total amount "d" in Formulas 9–11 above can be inter dispersed throughout the polymer (not necessarily in same concentrations) or all or majority of such polymeric unit can be concentrated in one particular location of the polymer.

Preferably the ratio of a:b:c:d:e:f is 0–20 mol %:0–50 mol %:0–50 mol %:0.1–30 mol %:0–10 mol %:0–50 mol %.

Preferably, photoresist polymers of the present invention comprise the first, second and third monomers defined above, e.g., a, b and d in photoresist polymers of formula 9–11 are not zero.

Preferred polymers of the present invention include polymers of the formula:

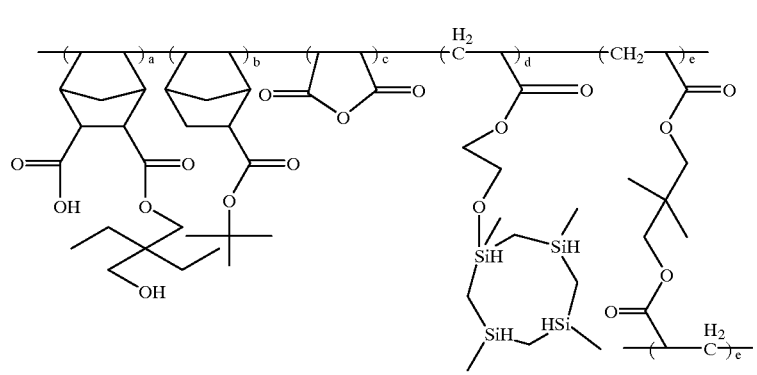

9A

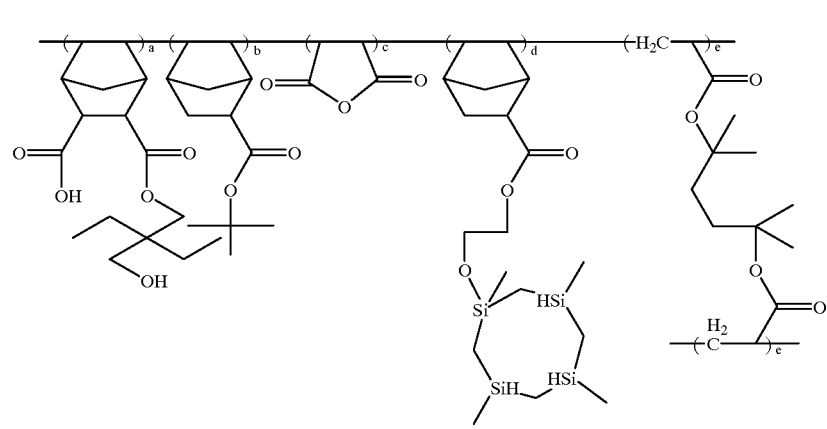

10A

; and

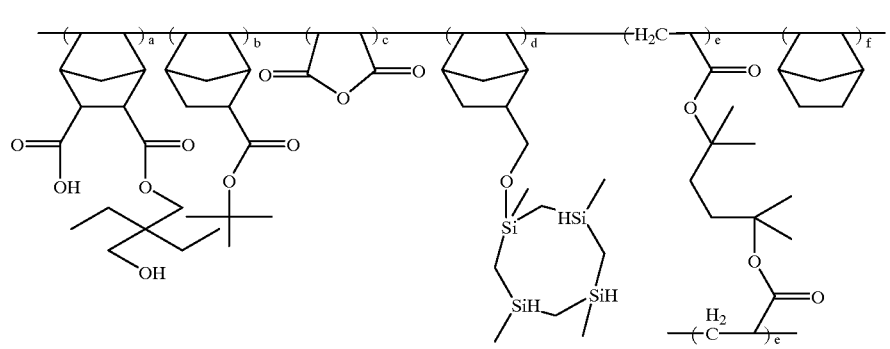

11A

Preferably, the molecular weight of photoresist polymers of the present invention is in the range of from about 3,000 to about 50,000, and more preferably from about 3,000 to about 20,000.

Photoresist polymers of the present invention can be prepared using a variety of methods including a radical polymerization of monomers with a conventional radical polymerization initiator. An exemplary procedure for pre paring polymers of the present invention includes the steps of:
(a) admixing
  (i) a monomer selected from the group consisting of compounds of Formulas 1 to 3, and mixtures thereof,
  (ii) another monomer selected from the group consisting of compounds of Formulas 5 to 8, and mixtures thereof,
  (iii) maleic anhydride, and
  (iv) a polymerization initiator; and
(b) polymerizing said admixture under conditions sufficient to produce said photoresist polymer, preferably in an inert atmosphere, e.g., nitrogen, argon or helium.

The polymerization process can be a bulk polymerization or a solution polymerization using any inert solvent. If a solution polymerization process is used, the polymerization solvent is preferably selected from the group consisting of tetrahydrofuran, dimethylformamide, chloroform, ethylacetate, acetone, ethylmethylketone, dimethylsulfoxide, dioxane, benzene, toluene, xylene, and mixtures thereof. In addition, when the polymer is prepared in a solid state, the polymerization solvent is selected from the group consisting of diethyl ether, petroleum ether, n-hexane, cyclohexane, methanol, ethanol, propanol and isopropyl alcohol, preferably diethyl ether, petroleum ether and n-hexane.

Exemplary polymerization initiator is selected from the group consisting of 2,2'-azobisisobutyronitrile (AIBN), benzoyl peroxide, acetyl peroxide, lauryl peroxide, tert-butylperoxide and bisazide compounds.

Polymerization reaction is typically performed at a temperature range of from about 50° C. to about 120° C., and preferably from about 50° C. to about 80° C. With a typical reaction time of from about 4 to about 24 hours.

The present invention also provides a photoresist composition comprising (i) a photoresist polymer described above, (ii) a photoacid generator, and (iii) an organic solvent.

Photoacid generators include onium type compounds, halogen compounds, diazoketone compounds, sulfone compounds and sulfonic acid compounds. More preferably, the onium type compounds containing sulfides and iodide are employed. In one particular embodiment of the present invention, the photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate, dibutylnaphthylsulfonium triflate, and mixtures thereof.

Typically, the amount of photoacid generator used is from about 0.05% by weight to about 10% by weight of the photoresist polymer. It has been found by the present inventors that when the amount of photoacid generator used is less than about 0.05%, the photosensitivity of the photoresist composition is significantly decreased. And when the amount of photoacid generator used is greater than about 10%, a poor pattern formation results, presumably due to its high absorption of deep ultra violet light (DUV).

The organic solvent is preferably selected from the group consisting of cyclohexanone, cyclopentanone, methyl 3-methoxypropionate, ethyl 3-ethoxypriopionate, propyleneglycol methyletheracetate, and mixtures thereof. The amount of the organic solvent used is preferably in the range of from about 500% by weight to about 2000% by weight of the photoresist polymer. When the amount of the solvent in the photoresist composition is about 1000% by weight of the polymer, a photoresist film having thickness of 0.2 $\mu$m can be readily obtained.

Another aspect of the present invention provides a process for forming a photoresist pattern using the photoresist composition described above. The process for forming a photoresist pattern includes the steps of:
(a) coating a photoresist composition described above on a substrate of a semiconductor element to form a photoresist film;
(b) exposing the photoresist film to light using a light source; and
(c) developing the photoresist film to produce the photoresist pattern, Photoresist compositions of the present invention can be used in a single layer photoresist pattern formation process as described above. Alternatively, photoresist compositions of the present invention can be used in a bilayer photoresist pattern formation process, which generally involves coating the semiconductor substrate with a bottom anti-reflective coating material (BARC), g-line photoresist or i-line photoresist to produce a lower layer film, and coating the lower layer film with the photoresist composition described above to produce an upper layer photoresist film.

The photoresist pattern formation process can further include the steps of heating (i.e., baking) the substrate before and/or after the step (b) described above. Moreover, in the bilayer photoresist pattern formation process, the baking step can be performed after forming the lower layer film.

In the single layer photoresist pattern formation process, the exposed photoresist film can be developed by contacting it with an alkaline developing solution under conditions sufficient to produce the photoresist pattern. In the bilayer photoresist pattern formation process, the exposed photoresist film can be developed by contacting the upper layer photoresist film with an alkaline solution under conditions sufficient to produce an upper layer photoresist pattern, and contacting the lower layer photoresist film with $O_2$ plasma using the upper layer photoresist pattern as a mask under conditions sufficient to produce the photoresist pattern. This bilayer photoresist pattern formation process is illustrated in FIG. 1, where the dry development is performed using $O_2$ plasma.

As illustrated in FIG. 1, a lower layer material 13, such as a bottom anti-reflective coating material (BARC), g-line photoresist or i-line photoresist, is coated on a wafer 11. Thereafter, the photoresist composition 15 of the present invention is coated on the lower layer material 13. The upper layer photoresist 15 is exposed to light using an exposure mask (A). Typically, the light source is ArF exposer ($\lambda$=193 nm), KrF exposer ($\lambda$=248 nm), VUV exposer ($\lambda$=157 nm), EUV exposer ($\lambda$=13 nm), E-beam or X-ray. The exposed upper layer photoresist film 15 is developed using 0.1 to 10 wt % aqueous tetramethylammonium hydroxide (TMAH) solution (B) to produce an upper layer photoresist pattern. Using the upper layer photoresist pattern as a mask, the lower layer material 13 is dry developed using $O_2$ plasma, thereby forming a lower layer material pattern. It is believed that during this $O_2$ plasma dry developing process, a silicon oxide film 17 is produced from the upper layer photoresist pattern which comprises the photoresist composition comprising silicon. The exposed lower layer material 13 and the silicon oxide film 17 is removed to form a photoresist pattern (C and D).

As discussed above, photoresist compositions of the present invention comprise a photoresist polymer which is derived from a relatively silicon rich photoresist monomer. Silicon present in photoresist compositions of the present invention (7 to 30% by weight of the photoresist polymer) forms a silicon dioxide film during a dry $O_2$ plasma etching process, thus providing a superior etching resistance. Therefore, even if a relatively inexpensive g-line or i-line photoresist, or general BARC is used as a lower layer film material, a photoresist pattern can be successfully produced using a thin film of photoresist composition of the present invention. For example, a photoresist film having a thickness of 2000 Å or less can be easily etched without the problems associated with conventional photoresist compositions. And since a thin photoresist film typically has a low light absorption, photoresist compositions of the present invention are useful in photolithography processes that use an ultrashort wavelength or an electron beam.

Yet another aspect of the present invention provides a semiconductor element manufactured using a photoresist composition described above.

Additional objects, advantages, and novel features of this invention will become apparent to those skilled in the art upon examination of the following examples thereof, which are not intended to be limiting.

EXAMPLES

I. PREPARATION OF PHOTORESIST MONOMERS

Example 1

Synthesis of ethylene glycol 2,4,6,8-tetramethylcyclotetrasiloxanyl ether acrylate To a solution containing 1M of 2,4,6,8-tetramethylcyclotetrasiloxane and 0.01 g of $(CH_3CO_2)_2Zn$ was slowly added 1M of 2-hydroxyethyl acrylate. The resulting mixture was stirred for 12 hours at a room temperature. Thereafter, 200 mL of benzene and 200 mL of cold water were added. The organic layer was separated, washed with 200 mL of cold water, dried over $MgSO_4$, filtered and concentrated by distillation to provide the title compound of Formula 1A (yield: 97%).

Example 2

Synthesis of ethylene glycol 2,4,6,8-tetramethylcyclotetrasiloxanyl ether 5-norbornene-2-carboxylate To a solution containing 1M of 2,4,6,8-tetramethylcyclotetrasiloxane and 0.01 g of $(CH_3CO_2)_2Zn$ was slowly added 1M of 2-hydroxyethyl-5-norbornene-2-carboxylate. The resulting mixture was stirred for 24 hours at a room temperature. Thereafter, 200 mL of benzene and 200 mL of cold water were added. The organic layer was separated, washed with 200 mL of cold water, dried over $MgSO_4$, filtered and concentrated by distillation to provide the title compound of Formula 1A (yield: 97%).

Example 3

Synthesis of (5-norbornene-2-methoxy)2,4,6,8-tetramethylcyclotetrasiloxane

The procedure of Example 1 was repeated using 1M of 5-norbornene-2-methanol instead of 1M of 2-hydroxyethyl acrylate to provide the title compound of Formula 3A (yield: 98%).

II. PREPARATION OF PHOTORESIST POLYMERS

Example 4

Synthesis of Poly{5-norbornene-2-(3-hydroxymethyl-3-ethyl)butyl carboxylate-3-carboxylic acid/tert-butyl 5-norbornene-2-carboxylate/maleic anhydride/neopentylglycol diacrylate/ethyleneglycol 2,4,6,8-tetramethylcyclotetrasiloxanyl ether acrylate}

To 200 mL of tetrahydrofuran was added 0.1 mole of 5-norbornene-2-(3-hydroxymethyl-3-ethyl)butyl carboxylate-3-carboxylic acid, 0.4 mole of tert-butyl 5-norbornene-2-carboxylate, 0.5 mole of maleic anhydride, 0.01 mole of neopentylglycol diacrylate, 0.1 mole of ethyleneglycol 2,4,6,8-tetramethylcyclotetrasiloxanyl ether acrylate, and 3 g of AIBN. The mixture was heated to 65° C. for 8 hours. Thereafter, ether/diethyl ether (2:1) solution was added to the reaction mixture and the solid was filtered and dried to provide the title polymer of Formula 9A (yield: 62%).

Example 5

Synthesis of Poly{5-norbornene-2-(3-hydroxymethyl-3-ethyl)butyl carboxylate-3-carboxylic acid/tert-butyl 5-norbornene-2-carboxylate/maleic anhydride/2,5-dimethyl-2,5-hexanediol diacrylate/ethyleneglycol 2,4,6,8-tetramethylcyclotetrasiloxanyl 5-norbornene-2-carboxylate}

The procedure of Example 4 was repeated using 0.1 mole of 5-norbornene-2-(3-hydroxymethyl-3-ethyl)butyl carboxylate-3-carboxylic acid, 0.4 mole of tert-butyl 5-norbornene-2-carboxylate, 0.5 mole of maleic anhydride, 0.01 mole of 2,5-dimethyl-2,5-hexanediol diacrylate, 0.1 mole of ethyleneglycol 2,4,6,8-tetramethylcyclotetrasiloxanyl 5-norbornene-2-carboxylate and 3 g of AIBN to provide the title polymer of Formula 10A (yield 58%).

Example 6

Synthesis of Poly{5-norbornene-2-(3-hydroxymethyl-3-ethyl)butyl carboxylate-3-carboxylic acid/tert-butyl 5-norbornene-2-carboxylate/maleic anhydride/2,5-dimethyl-2,5-hexanediol diacrylate/(5-norbornene-2-methoxy)2,4,6,8-tetramethylcyclotetrasiloxane/norbornene}

The procedure of Example 4 was repeated using 0.1 mole of 5-norbornene-2-(3-hydroxymethyl-3-ethyl)butyl carboxylate-3-carboxylic acid, 0.35 mole of tert-butyl 5-norbornene-2-carboxylate, 0.55 mole of maleic anhydride, 0.01 mole of 2,5-dimethyl-2,5-hexanediol diacrylate, 0.1 mole of (5-norbornene-2-methoxy)2,4,6,8-tetramethylcyclotetrasiloxane, 0.03 mole of norbornene and 3 g of AIBN to provide the title polymer of Formula 11A (yield: 61%).

III. PREPARATION OF PHOTORESIST COMPOSITION AND FORMATION OF PATTERN

Example 7

A photoresist composition was prepared by adding 10 g of photoresist polymer prepared in Example 4 and 0.12 g of triphenylsulfonium triflate to 150 g of ethyl 3-ethoxypropionate solvent, and filtering the resulting mixture through a 0.10 µm filter.

Figure 2:
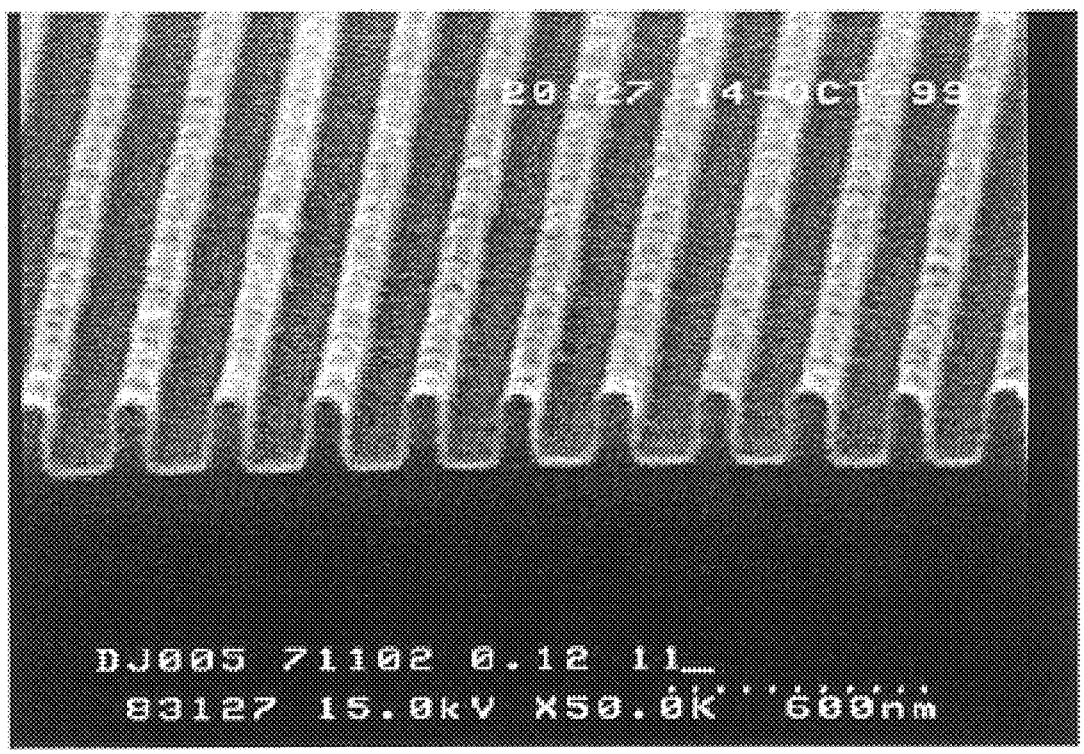
FIGS. 2 to 4 is a photograph showing patterns obtained in Examples 7 to 9.

I-line photoresist was coated on a silicon wafer to form a lower layer with a thickness of about 5000 Å. The coated silicon wafer was soft baked. Thereafter, 1 mL of the photoresist composition was spin coated on to the silicon wafer and baked at 130° C. for 90 seconds. The baked photoresist film was exposed to light using an ArF exposer and post-baked at 130° C. for 90 seconds [see FIG. 1(A)]. The exposed photoresist film was developed using a 2.38 wt % aqueous TMAH solution to produce an upper layer photoresist pattern [see FIG. 1(B)]. The lower layer photoresist was dry developed with $O_2$ plasma using the upper layer pattern as a mask to form a lower layer photoresist pattern. It was observed that during the $O_2$ plasma dry etching process a silicon oxide film was produced from the upper layer photoresist pattern containing silicon. The exposed lower layer photoresist and the silicon oxide film were removed [see FIGS. 1(C) and 1(D), respectively] providing a photoresist pattern of 0.12 μm L/S (see FIG. 2).

Example 8

Figure 3:
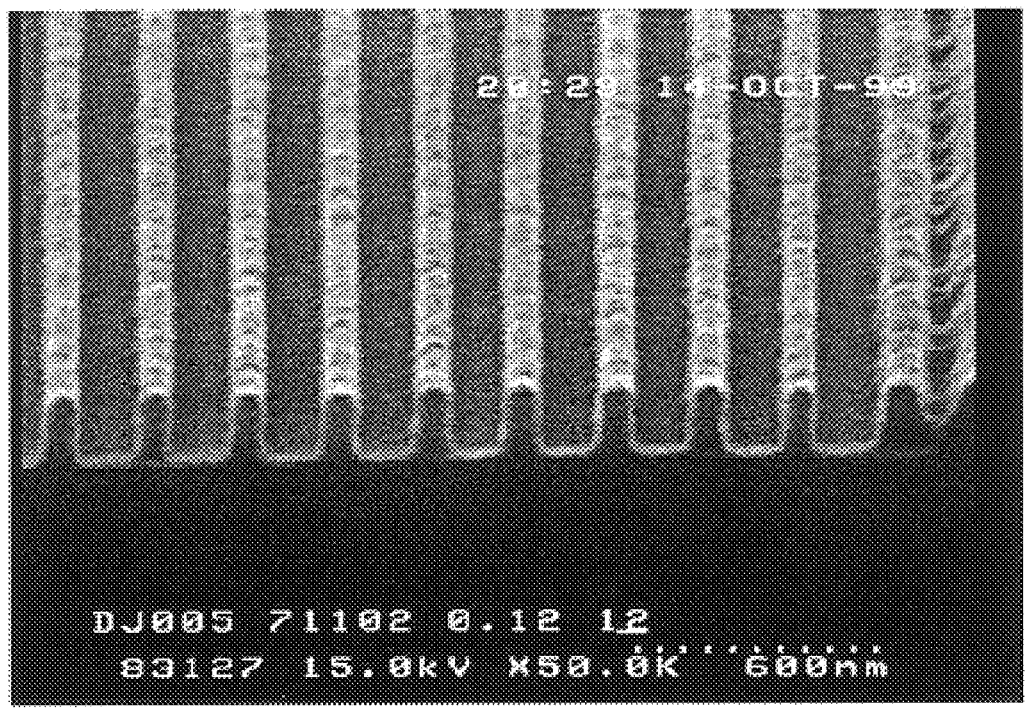

The procedure of Example 7 was repeated using 10 g of photoresist polymer prepared in Example 5 instead of photoresist polymer prepared in Example 4 to provide a photoresist pattern of 0.12 μm L/S (see FIG. 3).

Example 9

Figure 4:
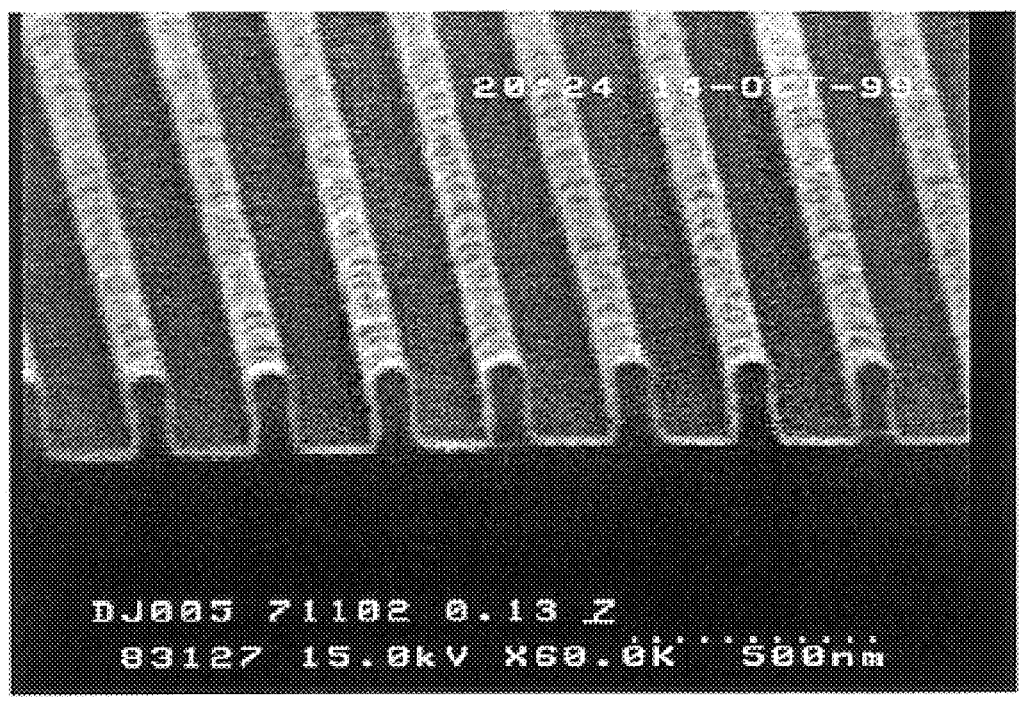

The procedure of Example 7 was repeated using 10 g of photoresist polymer prepared in Example 6 instead of photoresist polymer prepared in Example 4 to provide a photoresist pattern of 0.13 μm L/S (see FIG. 4).

As discussed above, photoresist compositions of the present invention are prepared using a silicon-rich photoresist monomer. The photoresist composition contains a proper amount of silicon, i.e., about 7 to about 30% by weight of the photoresist polymer. When etched by oxygen, the photoresist composition of the present invention forms a silicon oxide film resulting in a superior etching resistance relative to conventional photoresist compositions. Therefore, even if a relatively inexpensive g-line or i-line photoresist, or general BARC is used as a lower layer film material, a photoresist pattern can be successfully produced using a thin film of photoresist composition of the present invention, e.g., thickness of 2000 Å or less. Moreover, a bilayer photoresist pattern forming process can be used to produce a minute pattern without any significant pattern collapse resulting in a significant reduction in the production cost of semiconductor devices. Furthermore, a photoresist film having a thickness of 2000 Å or less can be easily etched without the problems associated with conventional photoresist compositions. And since a thin photoresist film typically has a low light absorption, photoresist compositions of the present invention are useful in photolithography processes that use an ultrashort wavelength or an electron beam.

In some embodiment, photoresist polymers of the present invention include diacrylate cross-linking monomers which increases the polymerization yield. This cross-linking can also improve a contrast ratio between the exposed region and the non-exposed region.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A photoresist polymer derived from a monomer comprising a first monomer selected from the group consisting of compounds of the formula:

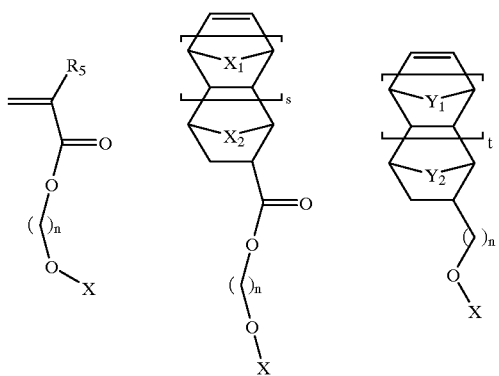

and mixtures thereof, wherein $X_1$, $X_2$, $Y_1$ and $Y_2$ are alkylene;

$R_5$ is hydrogen or alkyl;

s and t are integers from 0 to 2;

n is an integer from 1 to 5; and

X is a moiety of the formula:

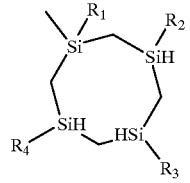

wherein each of $R_1$, $R_2$, $R_3$ and $R_4$ is independently hydrogen, $C_1$–$C_{10}$ alkyl, or $C_1$–$C_{10}$ alkyl comprising an ether linkage.

2. The photoresist polymer of claim 1, wherein each of $X_1$, $X_2$, $Y_1$ and $Y_2$ is independently methylene or ethylene.

3. The photoresist polymer of claim 1, wherein $R_5$ is hydrogen or methyl.

4. The photoresist polymer of claim 1, wherein said first monomer is selected from the group consisting of compounds of the formula:

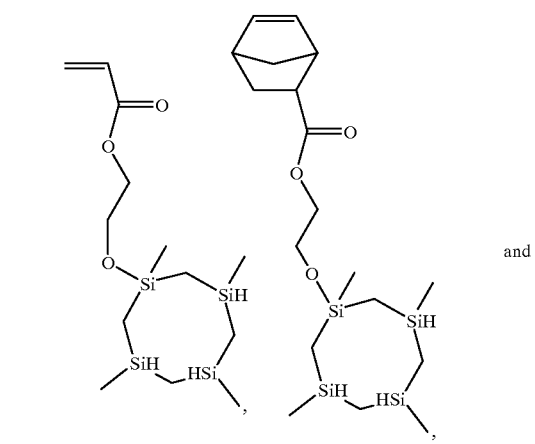

and

5. The photoresist polymer of claim 1, wherein the molecular weight of said photoresist polymer is in the range of from about 3,000 to about 50,000.

6. The photoresist polymer according to claim 1, wherein said monomer further comprises a second monomer of the formula:

wherein $V_1$ and $V_2$ are alkylene;

$R_6$ is an acid labile protecting group; and p is an integer from 0 to 2.

7. The photoresist polymer of claim 6, wherein each of $V_1$ and $V_2$ is independently methylene or ethylene.

8. The photoresist polymer of claim 6, wherein said acid labile protecting group is selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-yl.

9. The photoresist polymer according to claim 6, wherein said monomer further comprises a third monomer of the formula:

wherein $W_1$ and $W_2$ are alkylene;

$R_7$ is $C_1$–$C_{12}$ alkyl comprising an ether linkage or $C_1$–$C_{12}$ alkyl comprising a hydroxyl group; and q is an integer from 0 to 2.

10. The photoresist polymer of claim 9; wherein each of $W_1$ and $W_2$ is independently methylene or ethylene.

11. The photoresist polymer according to claim 9, wherein said monomer further comprises a cross-linking monomer of the formula:

wherein

Y is $C_1$–$C_{12}$ alkylene, oxygen, or $C_1$–$C_{12}$ alkylene comprising an ether linkage;

each of $R_8$ and $R_9$ is independently hydrogen or alkyl; and each of $R_{10}$, $R_{11}$, $R_{12}$ and $R_{13}$ is independently hydrogen, $C_1$–$C_{12}$ alkyl, or $C_1$–$C_{12}$ alkyl comprising an ether linkage.

12. The photoresist polymer of claim 11, wherein each of $R_8$ and $R_9$ is independently hydrogen or methyl.

13. The photoresist polymer of claim 11, wherein said monomer further comprises maleic anhydride.

14. The photoresist polymer of claim 13, wherein said monomer further comprises a sixth monomer of the formula:

wherein

Z is alkylene or oxygen.

15. The photoresist polymer of claim 14, wherein Z is methylene, ethylene or oxygen.

16. The photoresist polymer of claim 15, wherein said photoresist polymer is selected from the group consisting of polymers of the formula:

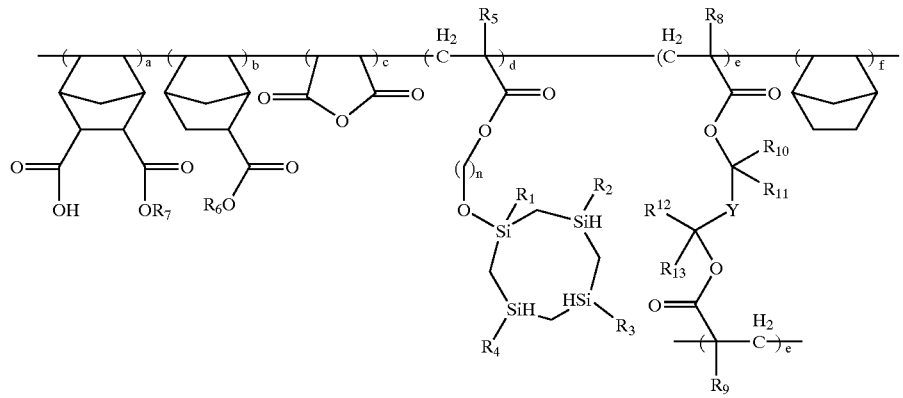

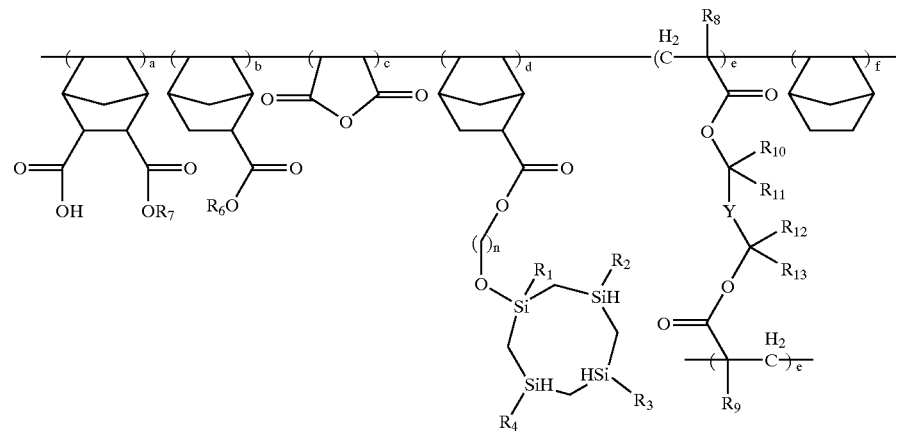

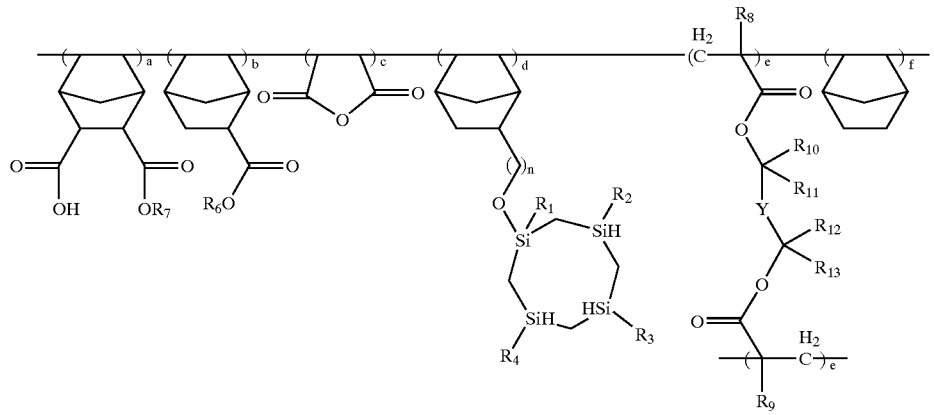

wherein
$R_1$, $R_2$, $R_3$, $R_4$, $R_5$, and n are those defined in claim 5;
$R_6$ is that defined in claim 9;
$R_7$ is that defined in claim 12;
$R_8$, $R_9$, $R_{10}$, $R_{11}$, $R_{12}$, $R_{13}$, and Y are those defined in claim 14; and
a, b, c, d, e and f individually denote a mole ratio of each monomer, provided the ratio of a:b:c:d:e:f is 0–20 mol %:0–50 mol %:0–50 mol %:0.1–30 mol %:0–10 mol %:0–50 mol %.

17. The photoresist polymer of claim 16, wherein each of $R_5$, $R_8$ and $R_9$ is independently hydrogen or methyl.

18. The photoresist polymer of claim 16, wherein said photoresist polymer is selected from the group consisting of compounds of the formula:

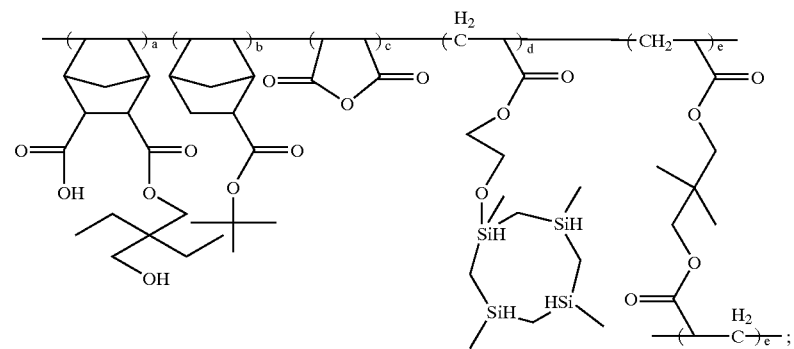
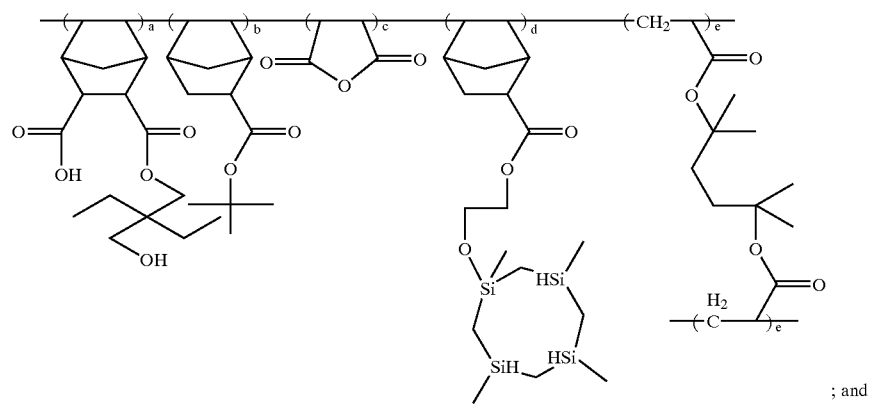
; and
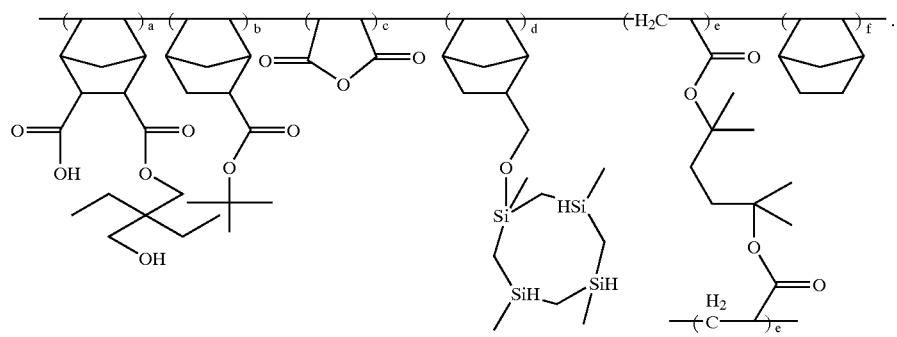
.
19. A photoresist composition comprising:
(i) photoresist polymer derived from a monomer comprising a first monomer selected from the group consisting of compounds of the formula:
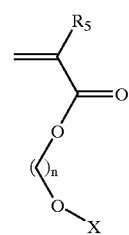
-continued
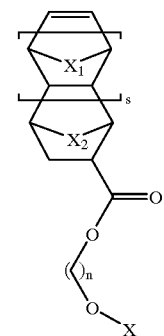

-continued

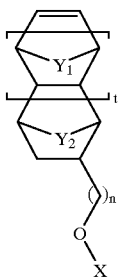

and mixtures thereof, wherein $X_1$, $X_2$, $Y_1$ and $Y_2$ are alkylene;

$R_5$ is hydrogen or alkyl;

s and t are integers from 0 to 2;

n is an integer from 1 to 5; and

X is a moiety of the formula:

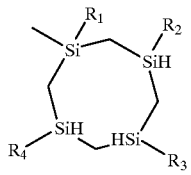

wherein
each of $R_1$, $R_2$, $R_3$ and $R_4$ is independently hydrogen, $C_1$–$C_{10}$ alkyl, or $C_1$–$C_{10}$ alkyl comprising an ether linkage;

(ii) a photoacid generator; and (iii) an organic solvent.

20. The photoresist composition of claim 19, wherein said photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate, dibutyl-naphthylsulfonium triflate, and mixtures thereof.

21. The photoresist composition of claim 19, wherein the amount of said photoacid generator is in the range from about 0.05 to about 10% by weight of said photoresist polymer.

22. The photoresist composition of claim 19, wherein said organic solvent is selected from the group consisting of cyclohexanone, cyclopentanone, methyl 3-methoxypropionate, ethyl 3-ethoxypriopionate, propyleneglycol methyletheracetate, and mixtures thereof.

23. The photoresist composition of claim 19, wherein the amount of said organic solvent is in the range of from about 500 to about 2000% by weight of said photoresist polymer.

* * * * *